United States Patent [19]

Muether et al.

[11] 4,193,002

[45] Mar. 11, 1980

[54] DENTAL X-RAY DIAGNOSTIC INSTALLATION

[75] Inventors: Manfred Muether; Tilman Phleps; Ernst Schmitt, all of Bensheim, Fed. Rep. of Germany

[73] Assignee: Siemens Aktiengesellschaft, Berlin & Munich, Fed. Rep. of Germany

[21] Appl. No.: 905,792

[22] Filed: May 15, 1978

[30] Foreign Application Priority Data

May 23, 1977 [DE] Fed. Rep. of Germany ....... 2723243

[51] Int. Cl.² ............................................. G03B 41/16
[52] U.S. Cl. .................................................. 250/479
[58] Field of Search ................... 250/439 P, 478, 479

[56] References Cited

U.S. PATENT DOCUMENTS

| 2,829,263 | 4/1958 | Butler | 250/479 |
| 2,946,892 | 7/1960 | Bas Taymaz | 250/439 P |

Primary Examiner—Craig E. Church
Attorney, Agent, or Firm—Hill, Van Santen, Steadman, Chiara & Simpson

[57] ABSTRACT

The invention relates to a dental x-ray diagnostic installation comprising an applicator capable of introduction into the mouth of a patient on which is arranged an exit window from which x-radiation emitted by an anode can issue and expose a panoramic x-ray film applied externally of the patient's mouth. Associated with the installation is a holding system with which the x-ray film is supported in a defined position relative to the applicator and to the patient's mouth.

12 Claims, 4 Drawing Figures

DENTAL X-RAY DIAGNOSTIC INSTALLATION

BACKGROUND OF THE INVENTION

The invention relates to a dental x-ray diagnostic installation containing a housing comprising an applicator capable of introduction into the mouth of a patient, and manifesting an exit window from which x-radiation emitted by an anode can issue and expose an x-ray film applied externally of the patient's mouth.

The preparation of dental film radiographs with an x-ray diagnostic installation of this type has hitherto proceeded in such a manner that the x-ray film is applied at a region of the face of the patient, at which a dental or jaw radiograph is to be provided, and is then manually held securely in place by the patient until completion of the radiograph. A radiographic technique such as this has as a consequence an increased radiation burden on the hand of the patient; additionally, due to incorrect or insufficient pressure-contacting of the film, radiographs can result which are erroneous or which cannot be diagnostically interpreted.

SUMMARY OF THE INVENTION

It is the object of the invention to eliminate these disadvantages; i.e., to provide a solution by which a radiation burden on the hands holding the film during the radiograph can be avoided, and which results in radiographs of a consistently uniform good quality.

In accordance with the invention, the object set forth is achieved by virtue of the fact that an apparatus for holding the x-ray film in a defined position relative to the applicator and the patient's mouth is provided. The advantage of this solution is that the radiographs can be effected without the aid of the patient, and that a reproduceable position of the x-ray film in relation to the x-ray tube is provided.

Advantageous further developments and embodiments of the invention are contained in the sub-claims. Two sample embodiments of the invention shall be explained in further detail in the following on the basis of the accompanying sheets of drawings; and other objects, features and advantages will be apparent from this detailed disclosure and from the appended claims.

DETAILED DESCRIPTION

Figure 1:
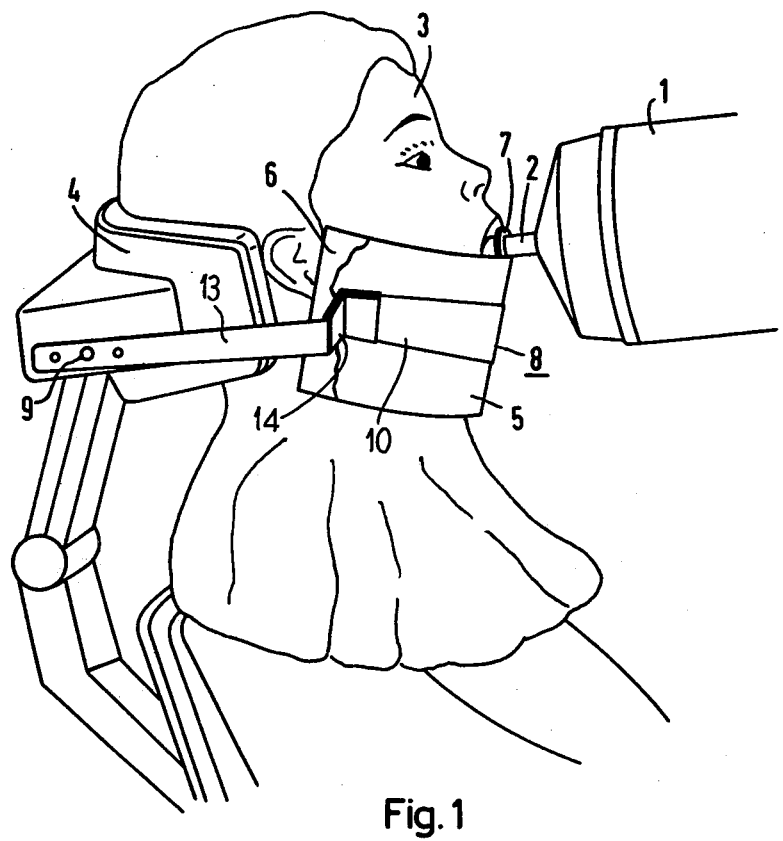
FIG. 1 is a somewhat diagrammatic perspective view illustrating an embodiment of the present invention in operative association with dental x-ray apparatus and a support for the patient's head.

In the x-ray diagnostic installation illustrated in FIG. 1, reference numeral 1 designates the housing of an x-ray apparatus in the interior of which an x-ray tube and the necessary associated parts, such as high voltage transformer, etc., are arranged. From the frontal end of housing 1, an applicator 2 projects which is introduced into the mouth of a patient. The patient's head 3 rests against a support 4 which is mounted in an articulated fashion to an examination chair which is not further designated. Reference numeral 5 denotes a film pocket in which an x-ray film 6 which is to be exposed is inserted. The film (here for a radiograph of the lower jaw) can be supported in the pocket without as well as with a layer protecting against exposure. In the first instance, it is necessary to insert the film into the pocket in a dark room. The film pocket 5 contains at its upper end, centrically disposed, a part 7 constructed in the shape of a loop which is placed over applicator 2 (which may have a constant diameter cylindrical surface without grooves; or may have the configuration shown at 20, 22, 23 in FIG. 3). In this way, a satisfactorily precise position of the film pocket—and hence of the film supported in the latter—is provided in relation to the x-ray tube; a lateral slipping out of place as well as an upward slipping out of place, but especially a downward slipping out of place is thereby prevented. In an upper jaw radiograph such as is illustrated in FIG. 3 the loop prevents an upward movement of the pocket and hence of the film relative to applicator 2.

Reference numeral 8 designates a holding part detachably arranged over film pocket 5 and which is detachably secured to the head support 4 by cooperating means such as a button 9 secured to the support 4 and multiple apertures or other adjustable connecting means along an elastic holding band 13. The elastic force can be varied for example through the arrangement of several holes along the length of holding band 13.

Figure 2:
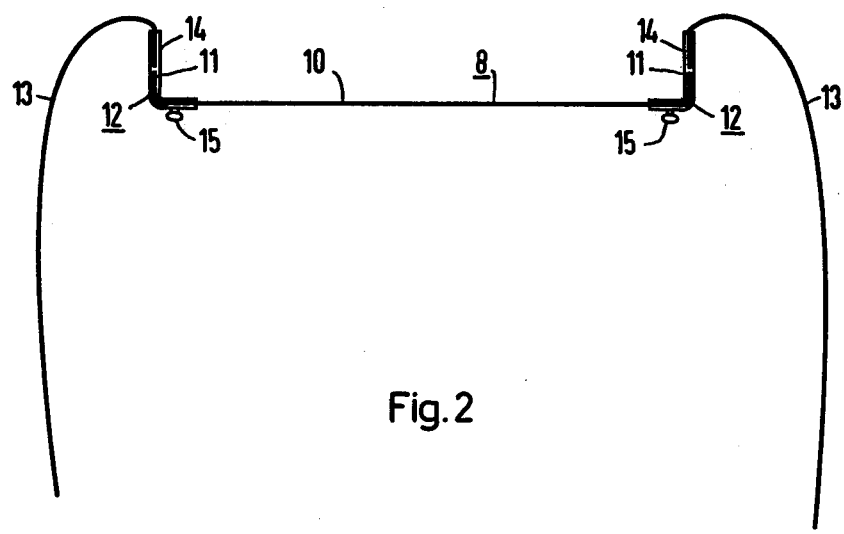
FIG. 2 is a somewhat diagrammatic plan view of a support part of the embodiment of FIG. 1, but shown in the non-applied state.

FIG. 2 illustrates the support part 8 in a plan view and in the non-applied state. In the non-applied state, support part 8 consists of a normally planar but flexible synthetic (or plastic) plate 10 with outwardly bent ends 11 which are mounted in angles 12 consisting of a more rigid material than plate 10. The ends of holding bands 13 are also secured in angles 12. Legs 14 of angles 12 point away from the patient's head in the applied state; namely, they are approximately radially directed (see FIG. 1). By this means, a good fit (or emplacement) of the exterior sections of the film pocket 5 and hence of the film 6 is achieved. Reference numeral 15 denotes fungiform-constructed buttons which are snapped into correspondingly constructed, non-illustrated recesses in the film pocket 5. One of the recesses is expediently constructed in the form of a longitudinal groove, (such as indicated at 24 in FIG. 4) in order, in this manner, to compensate relative movements between the film pocket 5 and synthetic plate 10 during emplacement of the film pocket on the patient's mouth. Through the described manner of mounting, a defined allocation of the support parts for the film pocket or the film, respectively, is provided. Hence, in connection with loop 7, a satisfactorily precise and reproduceable position of the film inserted in the film pocket in relation to the x-ray tube is achieved. Part 7 may be permanently secured at its periphery to pocket 5 and may have an inner diameter conforming to the outside diameter of applicator 2 (or with an applicator configuration as shown in FIG. 3, the part 7 may be of stretchable material so as to fit snugly in recess 23). Part 7 may also be constructed in the form of a hook or in the form of an open ring and may be fastened to applicator 2 (for example at the annular groove 23, FIG. 3) by means of a hooking or clasping effect (see portion 25, FIG. 4).

Figure 3:
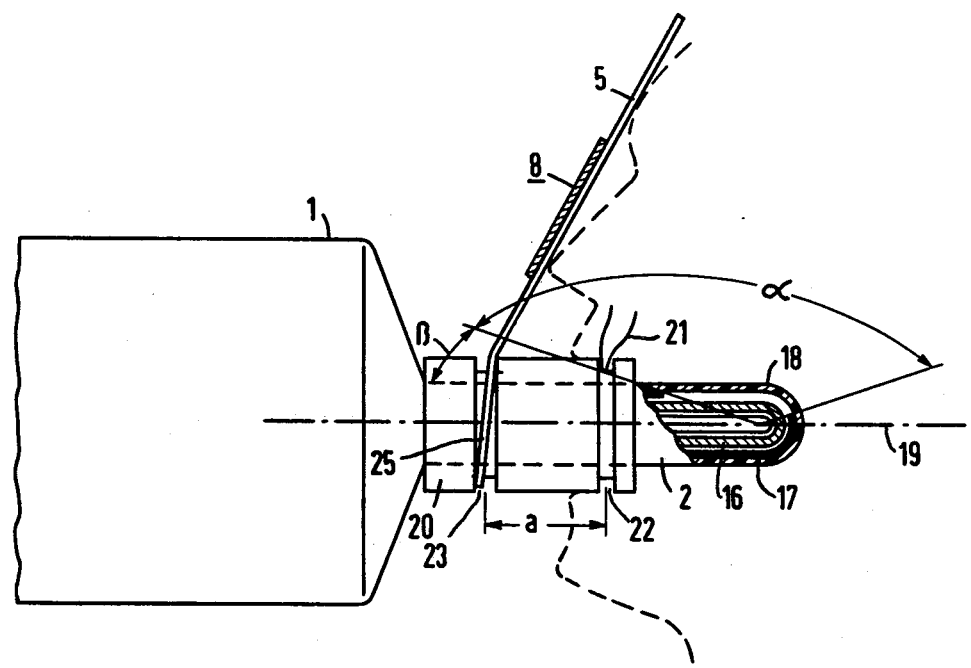
FIG. 3 is a partial somewhat diagrammatic side elevational view of a second embodiment of the invention, the x-ray applicator being broken away and shown in section, and illustrating on an enlarged scale details applicable to both of the embodiments.

FIG. 3 illustrates the x-ray diagnostic installation in longitudinal section with an applied film for radiographs of the upper jaw, or of adjacent regions. The internal construction of the applicator is recognizable from the illustration and is also applicable to the embodiment of FIGS. 1 and 2.

Applicator 2, which is inserted in the patient's mouth, encloses an anode 16 which is surrounded by a lead cap 17 with the exception of the desired angular range α. A synthetic tube 18 provides an outer enclosing surface. The x-rays produced at anode 16 issue over a field of conical configuration from the exit window, delimited as indicated by the angle α. Synthetic tube 18, together with lead cap 17, is rotatable about an axis 19, such that panoramic radiographs can be made of the upper jaw (FIG. 3) as well as of the lower jaw (FIG. 1). Reference numeral 20 denotes a so-called biting block which contains a first annular groove 22 in which the teeth 21 to be reproduced are placed. The purpose of the biting block is to raise the teeth beyond the dead radiation angle β such that they will always be completely reproduced on the film in the x-ray photograph. The biting block is constructed in the form of a cylindrical sleeve and is dimensioned in its structural height such that the emplacement surface engaged by the teeth 21 lies outside the boundary angle β.

Figure 4:
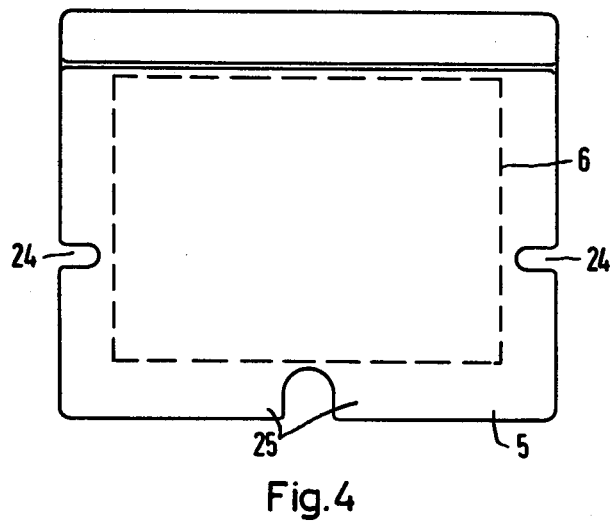
FIG. 4 illustrates a pocket for holding the x-ray film and illustrates side notches therein capable of detachable coupling with the support part of FIG. 2, but specifically illustrating a construction in accordance with the embodiment of FIG. 3.

Biting block 20 is provided at a spacial interval a (equal to 15 to 20 mm) with a second annular groove 23 into which marginal parts 25 of pocket 5 engage is a clasp-like manner (or said marginal parts may engage in groove 23 by virtue of being constructed in the manner of a complete ring 7, FIG. 1, or in the form of a slit or notched open ring). Marginal parts 25, in this fashion, hold the film in a defined position in relation to the teeth 21 as well as in relation to the applicator. FIG. 4, which illustrates film pocket 5 with the inserted film 6 in plan view, allows a good recognition of the marginal parts 25 formed e.g. by a punching-out operation. Reference numeral 24 designates slots arranged on both sides of the pocket into which the button-shaped holding parts 15 (FIG. 2) of the holding band 8 are snapped when the pocket with the film inserted therein is to be secured to the head of the patient.

For different penetration depths of the applicator (necessary in the case of adults or children), two lengths can be determined for the biting block. The one length can amount to e.g. 30 mm; the other, to 50 mm.

Instead of a fixation of the x-ray film, or of the pocket accommodating the film, on the applicator it is also possible to provide a fixation on the housing 1; for example, by means of a support mounting which is preferably pivotably supported on the latter.

It will be apparent that many modifications and variations may be effected without departing from the scope of the novel concepts and teachings of the present invention.

We claim as our invention:

1. A dental x-ray diagnostic installation of the type where x-rays are to originate exclusively from interiorly of the oral cavity, and comprising an applicator assembly including a housing and an applicator capable of insertion into the mouth of the patient which applicator exhibits an exit window from which x-radiation can issue and expose an x-ray film applied externally of the patient's mouth, characterized in a flexible x-ray film cassette (5) having first and second means (7; 8, 13) for removably holding the x-ray film (6) in a defined position relative to the applicator (2) and the patient's mouth, said first means (7) holding the x-ray film (6) in place by engagement with the applicator (2), and comprising a part having applicator-engaging means (7) in the form of a loop or hook configuration for at least partly encircling the applicator and for embracing opposite sides of the applicator to locate the x-ray film (6) relative to the applicator while conforming of the cassette to the patient both adjacent the applicator-engaging means and remote therefrom, and said second means comprising a support part (8) fixing the cassette (5) with the x-ray film (6) securely in place on the patient's mouth.

2. A dental x-ray diagnostic installation according to claim 1 with said applicator-engaging means comprising a loop configuration (7) for closely encircling said applicator for engaging on opposite sides of the applicator to locate the x-ray film relative to the applicator.

3. A dental x-ray diagnostic installation according to claim 1 with said applicator-engaging means comprising a hook configuration for engaging the applicator to locate the x-ray film relative to the applicator.

4. A dental x-ray diagnostic installation of the type where x-rays are to originate exclusively from interiorly of the oral cavity, and comprising an applicator assembly including a housing and an applicator capable of insertion into the mouth of the patient which applicator exhibits an exit window from which x-radiation can issue and expose an x-ray film applied externally of the patient's mouth, characterized in a flexible x-ray film cassette (5) having first and second means (25; 8, 13) for removably holding the x-ray film (6) in a defined position relative to the applicator (2) and the patient's mouth, said first means (25) holding the x-ray film (6) in place by engagement with the applicator (2), and comprising a part having applicator-engaging means in the form of a clasp-shaped configuration (25) for engaging on opposite sides of the applicator to locate the x-ray film (6) relative to the applicator while conforming of the cassette to the patient both adjacent the applicator-engaging means and remote therefrom, and said second means comprising a support part (8) fixing the cassette (5) with the x-ray film (6) securely in place on the patient's mouth.

5. A dental x-ray diagnostic installation according to claim 1 or claim 4, characterized in the support part (8) being provided with a holding band (13) having adjustment means for adjustment of its effective length, said support part (8) resting against the cassette (5) accommodating said film for holding the cassette in conforming engagement with the patient.

6. A dental x-ray diagnostic installation according to claim 5, characterized in the holding means commprising a non-stretchable flexible strip (10) having holding bands (13) mounted on both sides, and operable for holding the x-ray film (6) relative to the patient's head, the strip (10) being secured to at least one of the holding bands (13) by means of an angle (12) consisting of more rigid material than the strip (10), whereby a leg (14) of the angle (12) is directed approximately radially away from the patient's head (3) when the device is applied on the patient's head.

7. A dental x-ray diagnostic installation according to claim 6, characterized in that the support part (8) including said strip (10) and having connection means (15) for detachable connection to the cassette (5) accommodating the film (6).

8. A dental x-ray diagnostic installation according to claim 7, characterized in that, in order to effect a detachable connection, said connection means comprises fungiform-constructed attachment buttons (15) which fit into correspondingly constructed recesses (24) associated with the cassette (5).

9. A dental x-ray diagnostic installation according to claim 1 or claim 4, characterized in that said cassette (5) accommodating said film (6) is capable of being fixed relative to a biting block (20) capable of being mounted on the applicator (2).

10. A dental x-ray diagnostic installation according to claim 9, characterized in that, in order to effect fixation the biting block (20) has an annular groove (23) into which, in the applied state, clasp-shaped marginal parts (25) of the applicator-engaging means engage.

11. A dental x-ray diagnostic installation according to claim 9, characterized in that the biting block (20) is constructed in the form of a sleeve.

12. A dental x-ray diagnostic installation according to claim 9, characterized in that, in order to securely position in place the teeth (21) which are to be reproduced, the biting block (20) is provided with an annular groove (22) arranged at a defined distance (a) from the fixation point of the cassette-engaging means (25).

* * * * *